United States Patent
Yu et al.

(10) Patent No.: US 10,155,116 B2
(45) Date of Patent: Dec. 18, 2018

(54) SYSTEMS AND METHODS FOR STIMULATION SITE SELECTION

(71) Applicant: Cardiac Pacemakers, Inc., St. Paul, MN (US)

(72) Inventors: Yinghong Yu, Shoreview, MN (US); Martin McDaniel, San Diego, CA (US); Jason Humphrey, New Brighton, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 55 days.

(21) Appl. No.: 15/215,074

(22) Filed: Jul. 20, 2016

(65) Prior Publication Data

US 2017/0021175 A1 Jan. 26, 2017

Related U.S. Application Data

(60) Provisional application No. 62/196,728, filed on Jul. 24, 2015, provisional application No. 62/196,772, filed on Jul. 24, 2015.

(51) Int. Cl.
*A61N 1/368* (2006.01)
*A61N 1/02* (2006.01)
(Continued)

(52) U.S. Cl.
CPC ........... *A61N 1/3684* (2013.01); *A61N 1/025* (2013.01); *A61N 1/3627* (2013.01);
(Continued)

(58) Field of Classification Search
CPC .... A61N 1/3622; A61N 1/368; A61N 1/3684; A61N 1/36842; A61N 1/36843
See application file for complete search history.

(56) References Cited

U.S. PATENT DOCUMENTS

| | | | |
|---|---|---|---|
| 7,620,452 | B1 | 11/2009 | Russie |
| 8,055,343 | B2 | 11/2011 | Gandhi et al. |

(Continued)

FOREIGN PATENT DOCUMENTS

WO WO-2017019403 A1 2/2017

OTHER PUBLICATIONS

"International Application Serial No. PCT/US2016/043118, International Preliminary Report on Patentability dated Feb. 8, 2018", 7 pgs.

(Continued)

*Primary Examiner* — Allen Porter, Jr.
(74) *Attorney, Agent, or Firm* — Schwegman Lundberg & Woessner, P.A.

(57) ABSTRACT

Systems and methods for selecting one or more sites at or within at least one heart chamber for cardiac stimulation are disclosed. The system can include a physiologic sensor circuit to sense physiologic signals at two or more candidate stimulation sites. The system can generate respective activation timing indicators corresponding to the two or more candidate stimulation sites, and detect MI indicators indicating the presence of, or spatial proximity of each of the two or more candidate stimulation sites to a MI tissue. The system can use the activation timing indicators and the MI indicators to select at least one target stimulation site or to determine an electrostimulation vector. The system can display the selected target stimulation site to a user, or deliver electrostimulation to the patient at the target stimulation site or according to the determined electrostimulation vector.

20 Claims, 7 Drawing Sheets

(51) Int. Cl.
*A61N 1/372* (2006.01)
*A61N 1/362* (2006.01)
*A61N 1/37* (2006.01)
*A61N 1/365* (2006.01)

(52) U.S. Cl.
CPC ....... *A61N 1/3686* (2013.01); *A61N 1/36585* (2013.01); *A61N 1/3704* (2013.01); *A61N 1/3708* (2013.01); *A61N 1/37247* (2013.01)

(56) References Cited

U.S. PATENT DOCUMENTS

| | | |
|---|---|---|
| 2005/0137631 A1 | 6/2005 | Yu et al. |
| 2010/0274321 A1 | 10/2010 | Libbus |
| 2013/0131750 A1* | 5/2013 | Stadler ................ A61N 1/3627 607/25 |
| 2013/0131751 A1* | 5/2013 | Stadler ................ A61N 1/3684 607/25 |

OTHER PUBLICATIONS

"International Application Serial No. PCT/US2016/043118, International Search Report dated Nov. 23, 2016", 4 pgs.
"International Application Serial No. PCT/US2016/043118, Written Opinion dated Nov. 23, 2016", 5 pgs.

* cited by examiner

FIG. 7A

| ELECTROSTIMULATION VECTORS Δ/∇ | MI INDICATION Δ/∇ | THERAPY EFFICACY INDICATOR Δ/∇ | LONGEVITY INDICATOR Δ/∇ | COMPLICATION INDICATOR Δ/∇ |
|---|---|---|---|---|
| ☑ LV1-CAN | REMOTE/ABSENCE | 9 | 8 YEARS | 8 VOLTS |
| ☐ LV1-LV4 | PROXIMAL | 9 | 7.5 YEARS | 5 VOLTS |
| ☐ LV2-CAN | REMOTE/ABSENCE | 8 | 8 YEARS | 7 VOLTS |
| ☐ LV1-LV2 | REMOTE/ABSENCE | 8 | 4 YEARS | 4 VOLTS |
| ☐ LV4-CAN | PROXIMAL | 6 | 5 YEARS | 9 VOLTS |

FIG. 7B

| ELECTROSTIMULATION VECTORS Δ/∇ | LV AMPLITUDE Δ/∇ | RV-LV DELAY Δ/∇ | Q-LV DELAY Δ/∇ | CAPTURE THRESHOLD Δ/∇ | LEAD IMPEDANCE Δ/∇ | EST. BATTERY LIFE Δ/∇ | PNS THRESHOLD Δ/∇ |
|---|---|---|---|---|---|---|---|
| ☑ LV1-CAN | 1.5 mV | 111 ms | 120 ms | 1.7 V | 350 ohms | 8 YEARS | 8 VOLTS |
| ☐ LV1-LV4 | 0.7 mV | 101 ms | 110 ms | 1.5 V | 400 ohms | 7.5 YEARS | 5 VOLTS |
| ☐ LV2-CAN | 1.5 mV | 81 ms | 110 ms | 1.7 V | 400 ohms | 8 YEARS | 7 VOLTS |
| ☐ LV1-LV2 | 1.3 mV | 101 ms | 110 ms | 2.1 V | 550 ohms | 4 YEARS | 4 VOLTS |
| ☐ LV4-CAN | 0.5 mV | 81 ms | 100 ms | 1.7 V | 450 ohms | 5 YEARS | 9 VOLTS |

ND METHODS FOR
SYSTEMS AND METHODS FOR STIMULATION SITE SELECTION

CLAIM OF PRIORITY

This application claims the benefit of priority under 35 U.S.C. § 119(e) of U.S. Provisional Patent Application Ser. No. 62/196,728, filed on Jul. 24, 2015, and U.S. Provisional Patent Application Ser. No. 62/196,772, filed on Jul. 24, 2015, each of which is herein incorporated by reference in its entirety.

TECHNICAL FIELD

This document relates generally to medical devices, and more particularly, to devices and methods for electrostimulation of excitable tissues.

BACKGROUND

Congestive heart failure (CHF) is a leading cause of death in the United States. CHF occurs when the heart is unable to adequately supply enough blood to maintain a healthy physiological state. CHF can be treated by drug therapy, or by an implantable medical device (IMD) such as for providing cardiac pacing therapies, including resynchronization therapy (CRT) to correct cardiac dyssynchrony within a ventricle or between ventricles.

The IMD can chronically stimulate excitable tissues or organs, such as a heart, to treat abnormal cardiac rhythms or to help improve cardiac performance in a patient with CHF. Such ambulatory medical devices can have at least first and second electrodes that can be positioned within the heart or on a surface of the heart for contacting the cardiac tissue. The electrodes can be electrically coupled to an electronics unit such as a pulse generator, such as via a lead, and can be used to deliver one or more electrostimulations to the heart, such as to restore or to improve the normal heart function.

Overview

Cardiac stimulation using an implantable medical device (IMD) can involve one or more implantable electrodes that can be associated with one of the heart chambers, such as an atrium or a ventricle. Stimulation of the heart can be accomplished through myocardium stimulation using at least first and second electrodes that can be electrically connected to the IMD and in close contact with the cardiac tissue. The electrodes can, in some examples, be positioned along one or more implantable leads. The stimulation can be provided at specified stimulation strength (e.g., stimulation energy) sufficient to capture the heart tissue, that is, the stimulation can effectively cause depolarization propagating to a part or the entirety of the heart.

During the CRT therapy, synchronized stimulation can be applied to the left ventricle (LV) and the right ventricle (RV) of a heart. Conventionally, there can be one RV pacing site and one LV pacing site. Stimulation of multiple sites on a chamber of the heart, such as pacing at multiple LV sites (which is known as multisite LV pacing), has been proposed as an alternative to the conventional single site CHF therapy. Compared to the CRT therapy with single site LV pacing, multisite LV pacing may be more beneficial to some patients for various reasons, one of which may be its more effective recruitment of excitable cardiac tissues. Such benefits can include improved cardiac hemodynamic outcome in some CHF patients. The multisite pacing can involve electrostimulation delivered at two or more sites in at least one heart chamber (such as the LV) within a cardiac cycle.

Both the single site and multisite pacing can involve selecting, from a number of candidate pacing sites on a heart chamber, at least one pacing site for delivering electrostimulation. To achieve desired therapeutic outcome of restoring or improving a patient's cardiac function, careful assessment of a number of clinical factors and device parameters corresponding to various candidate pacing sites is beneficial. Additionally, effective pacing sites can be affected by a variety of factors including lead or electrode positioning at the heart, configurations of the pacing vector, values of stimulation parameters, pathophysiology of the heart such as myocardial infarction, growth of fibrous tissue or scar tissue around the electrode, lead integrity, and progression of cardiac disease or change in health condition, among others. As a result, a previously identified pacing site or a pacing vector may not provide desired or adequate electrostimulation therapy in the patient.

The present inventors have recognized that when the single site or multisite pacing is performed at a site that is within or in close proximity to an myocardial infarction (MI) tissue, a scar or fibrous tissue, a tissue of prolonged ischemia, or any other tissue with pathologically slow electrical conductivity or functional block, stimulation at these sites may not cause propagation of electrical activation to other parts of the cardiac tissue, and therefore may not achieve desired therapeutic outcome. For at least these reasons, the present inventors have recognized that there remains a demand for improved systems and methods for identifying proper pacing sites for use in single site or multisite cardiac stimulation, so as to improve the therapy outcome.

This document discusses, among other things, a system for selecting one or more sites at or within the heart for cardiac stimulation. The system can sense physiologic signals at two or more candidate stimulation sites, use the sensed physiologic signals to produce respective activation timing indicators corresponding to the two or more candidate stimulation sites. The system can additionally use the sensed respective physiologic signals to detect MI indicators that indicate presence of, or spatial proximity of each of the two or more candidate stimulation sites to, a MI tissue. The system can additionally detect one or more second indicators indicative of therapy efficacy, battery longevity, or complication of the electrostimulation vector. By using the activation timing indicators and the MI indicators, or together with one or more second indicators, the system can select, automatically or based on a user input, at least one target stimulation site from the two or more candidate stimulation sites. The system can generate a selectable set of candidate electrostimulation vectors including electrodes positioned at the at least one target stimulation site. The system can display the selected target stimulation site to a user, or deliver electrostimulation to the patient using the selected at least one target stimulation site.

In Example 1, a system can comprise a physiologic sensor circuit that includes a sense amplifier circuit to sense respective physiologic signals at two or more candidate stimulation sites at or within at least one chamber of a heart of a patient. The system can include an activation timer circuit and a myocardial infarction (MI) receiver circuit. The activation timer circuit can include a clock circuit coupled to the physiologic sensor circuit to use the sensed respective physiologic signals to produce respective activation timing indicators corresponding to the two or more candidate stimulation sites. The MI receiver circuit can receive respective MI indicators indicative of presence of, or relative spatial proximity of each of the two or more candidate stimulation sites to, a MI tissue. The system can include a stimulation site selector circuit that is communicatively coupled to the activation timer circuit and the MI detector circuit. The stimulation site selector circuit can select, automatically or based on a user input, at least one target stimulation site from the two or more candidate stimulation sites using the respective activation timing indicators and the respective MI indicators. The stimulation site selector circuit can generate a human-perceptible presentation of the two or more candidate stimulation sites with at least some of the respective MI indicators for selection of the at least one target stimulation site.

Example 2 can include, or can optionally be combined with the subject matter of Example 1, to optionally include a therapy circuit that can deliver electrostimulation to the patient using the selected at least one target stimulation site.

Example 3 can include, or can optionally be combined with the subject matter of Example 2, to include the stimulation site selector circuit which can select a first and a different second target stimulation sites from the two or more candidate stimulation sites using the respective activation timing indicators and the respective MI indicators. Example 3 can include the therapy circuit that can deliver the electrostimulation at the first and the second target stimulation sites during a same cardiac cycle.

Example 4 can include, or can optionally be combined with the subject matter of one or any combination of Examples 1 through 3 to include: the physiologic sensor circuit that can sense the respective physiologic signals including cardiac electrical signals sensed at two or more left-ventricular (LV) candidate sites of the heart; and the activation timer circuit that can determine the respective activation timing indicators including respective depolarization timings at the two or more LV candidate sites.

Example 5 can include, or can optionally be combined with the subject matter of Example 4, to optionally include the physiologic sensor circuit that can sense the cardiac electrical signals including intrinsic depolarizations at the two or more LV candidate sites Example 6 can include, or can optionally be combined with the subject matter of Example 4, to optionally include the physiologic sensor circuit that can sense the cardiac electrical signals including evoked depolarizations at the two or more LV candidate sites of the heart in response to a stimulation of one of a right ventricle (RV), a right atrium (RA), or a left ventricle (LV) of the heart.

Example 7 can include, or can optionally be combined with the subject matter of Example 4, to optionally include the activation timer circuit that can determine the respective depolarization timings including time intervals between a reference time and the respective depolarizations at the two or more LV candidate sites.

Example 8 can include, or can optionally be combined with the subject matter of Example 7, to optionally include the activation timer circuit that can detect the reference time including timing of a Q wave of a QRS complex. The activation timer circuit can determine the time intervals including Q-LV intervals.

Example 9 can include, or can optionally be combined with the subject matter of Example 7, to optionally include the activation timer circuit that can detect the reference time including timing of a sensed or paced activation at the RV. The activation timer circuit can determine the time intervals including RV-LV intervals.

Example 10 can include, or can optionally be combined with the subject matter of one or any combination of Examples 1 through 9 to include the MI detector circuit that can detect the respective MI indicators at the two or more candidate stimulation sites using the respective physiologic signals including cardiac electrical signals at two or more LV candidate sites.

Example 11 can include, or can optionally be combined with the subject matter of Example 10 to optionally include the MI detector circuit that can include a level detector circuit to determine, for each of the two or more LV candidate sites, an amplitude of the cardiac electrical signal sensed at the corresponding LV candidate site. The MI detector circuit can detect the MI indicator at the corresponding LV candidate site in response to the corresponding amplitude of the cardiac electrical signal meeting a specified criterion.

Example 12 can include, or can optionally be combined with the subject matter of Example 11 to optionally include the MI detector circuit that can include a comparator circuit to compare the amplitudes of the cardiac electrical signals to a threshold. The MI detector circuit can detect, for each of the two or more LV candidate sites, a respective MI indicator as one of a first indicator of being spatially proximal to a MI tissue if the determined amplitude falls below the threshold, or a second indication of being spatially remote to, or absence of, a MI tissue if the determined amplitude exceeds the threshold.

Example 13 can include, or can optionally be combined with the subject matter of one or any combination of Examples 1 through 12 to include the stimulation site selector circuit that can include a first comparator circuit to compare the detected MI indicators and a second comparator circuit to compare the activation timing indicators. The stimulation site selector can select the at least one target stimulation site using the comparison among the detected MI indicators and the comparison among the activation timing indicators.

Example 14 can include, or can optionally be combined with the subject matter of Example 13 to optionally include the stimulation site selector that can select the at least one target stimulation site associated with (1) the respective activation timing indicator indicating the at least one target stimulation site activating later than other of the two or more candidate stimulation sites, and (2) respective MI indicators indicating the at least one target stimulation site being spatially remote to a MI tissue.

In Example 15, a system can include: a physiologic sensor circuit that includes a sense amplifier circuit to sense cardiac electrical signals at two or more candidate stimulation sites in a left ventricle (LV) of a heart of a patient, an activation timer circuit that includes a clock circuit coupled to the physiologic sensor circuit to use the sensed cardiac electrical signals to produce respective activation timing indicators corresponding to the two or more LV candidate sites; a myocardial infarction (MI) detector circuit that can include a level detector circuit to determine, for each of the two or more LV candidate sites, an amplitude of the cardiac electrical signal sensed at the corresponding LV candidate site, and a comparator circuit that can compare the amplitudes of the cardiac electrical signals to a threshold to detect, for each of the two or more LV candidate sites, a respective MI indicator as one of a first indicator of being spatially proximal to a MI tissue if the determined amplitude falls below the threshold, or a second indication of being spatially remote to, or absence of, a MI tissue if the determined amplitude exceeds the threshold. The system can include a stimulation site selector circuit, communicatively coupled to the activation timer circuit and the MI detector circuit that can select, automatically or based on a user input, at least one target stimulation site from the two or more candidate stimulation sites. The at least one target stimulation site can be associated with (1) respective activation timing indicators indicating the at least one target stimulation site activating later than other of the two or more candidate stimulation sites, and (2) respective MI indicators indicating the at least one target stimulation site being spatially remote to a MI tissue. The system can include a therapy circuit that can deliver electrostimulation to the patient using the selected at least one target stimulation site.

In Example 16, a method can comprise the operations of: sensing, at two or more candidate stimulation sites at or within at least one chamber of a heart of a patient, respective physiologic signals; determining respective activation timing indicators corresponding to the two or more candidate stimulation sites by using the sensed respective physiologic signals; detecting respective myocardial infarction (MI) indicators indicating presence of, or relative spatial proximity of each of the two or more candidate stimulation sites, to a MI tissue; selecting at least one target stimulation site from the two or more candidate stimulation sites using the respective activation timing indicators and the respective MI indicators; and generating human-perceptible presentation of the two or more candidate stimulation sites with at least some of the respective MI indicators for selection of the at least one target stimulation site.

Example 17 can include, or can optionally be combined with the subject matter of Example 16, to optionally include an operation of delivering electrostimulation using the selected at least one target stimulation site.

Example 18 can include, or can optionally be combined with the subject matter of Example 17, to optionally include operations of selecting the at least one target stimulation site that can include selecting at least a first and a different second target stimulation sites from the two or more candidate stimulation sites using the respective activation timing indicators and the respective MI indicators; and delivering the electrostimulation that can include delivering respective electrostimulation at the first and the second target stimulation sites during a same cardiac cycle.

Example 19 can include, or can optionally be combined with the subject matter of Example 16, to optionally include options of sensing the respective physiologic signals that can include sensing cardiac electrical signals at two or more left-ventricular (LV) candidate sites of the heart, and determining the respective activation timing indicators that can include determining respective depolarization timings at the two or more LV candidate sites.

Example 20 can include, or can optionally be combined with the subject matter of Example 19, to optionally include an operation of determining the respective activation timing indicators that can include determining time intervals between a reference time and the respective depolarization timings at the two or more LV candidate sites. The reference timing can include timing of a Q wave of a QRS complex or timing of a sensed or paced activation at a right ventricle (RV).

Example 21 can include, or can optionally be combined with the subject matter of Example 16, to optionally include an operation of sensing the respective physiologic signals that can include sensing cardiac electrical signals at two or more left-ventricular (LV) candidate sites of the heart, and determining the respective MI indicators that can include determining amplitudes of the cardiac electrical signals sensed at the two or more LV candidate sites; comparing the amplitudes of the cardiac electrical signals to a threshold; and detecting, for each of the two or more LV candidate sites, a respective MI indicator as one of a first indicator of being spatially proximal to a MI tissue if the determined amplitude falls below a threshold, or a second indication of being spatially remote to, or absence of, a MI tissue if the determined amplitude exceeds the threshold.

Example 22 can include, or can optionally be combined with the subject matter of Example 16, to optionally include the operations of selecting the at least one target stimulation site, which can include selecting the at least one target stimulation site associated with (1) respective activation timing indicators indicating the at least one target stimulation site activating later than other of the two or more candidate stimulation sites, and (2) respective MI indicators indicating the at least one target stimulation site being spatially remote to a MI tissue.

Example 23 can include, or can optionally be combined with the subject matter of one or any combination of Examples 1 through 14 to include, the stimulation site selector circuit that can be configured to generate a selectable set of candidate electrostimulation vectors including electrodes positioned at the at least one target stimulation site.

Example 24 can include, or can optionally be combined with the subject matter of Example 23 to optionally include, a secondary indicator generation circuit and a user interface. The secondary indicator generation circuit can be configured to generate one or more second indicators indicative of one of therapy efficacy, battery longevity, or complication of stimulation. The user interface enables a user to rank the at least some of the candidate electrostimulation vectors according to an order of the MI indicators or the one or more second indicators, to select at least one target electrostimulation vector from the candidate electrostimulation vectors, or to program an electrostimulation therapy for delivery at the heart according to the selected at least one target electrostimulation vector.

Example 25 can include, or can optionally be combined with the subject matter of Example 24 to optionally include, the user interface that enables a user to rank the at least some of the candidate electrostimulation vectors, wherein the ranking can include generating first ranked vectors by ranking the at least some of the plurality of candidate electrostimulation vectors according to a first specified order of first specified indicators, and generating at least second ranked vectors by ranking at least a portion of the first ranked vectors according to a second specified order of second specified indicators, the portion of the first ranked vectors having corresponding first indicators meeting a specified condition. The first specified indicators can be different from the second specified indicators, and the first and second specified indicators can each be selected from MI indicators, therapy efficacy indicators, battery longevity indicators, or complication indicators.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 7A-B illustrate generally examples of display of electrostimulation vectors and various corresponding indicators.

DETAILED DESCRIPTION

Disclosed herein are systems, devices, and methods for determining at least one site in at least one chamber of a heart for therapeutic stimulation. The stimulation, such as an electrostimulation sequence, can be applied to one or more sites of the heart such as at a left ventricle (LV) of the heart, to restore or improve cardiac performance. The physiologic signals sensed at multiple sites during cardiac electrostimulation at a specified site or when the heart undergoes a specified condition, such as during an intrinsic heart rhythm, can be analyzed to determine at least one target stimulation site. The selected stimulation sites can be stimulated simultaneously or asynchronously within a cardiac cycle to achieve desired cardiac hemodynamics.

Figure 1:
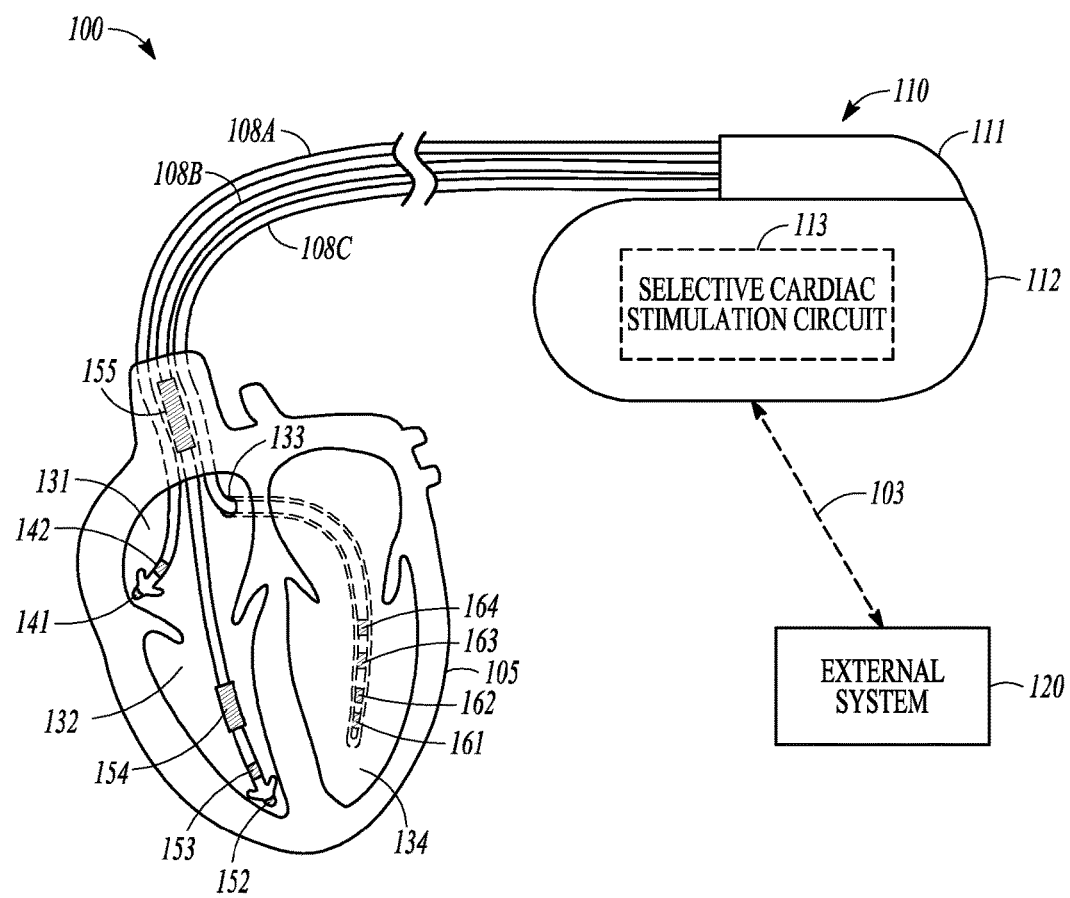
FIG. 1 illustrates generally an example of a Cardiac Rhythm Management (CRM) system and portions of an environment in which the CRM system can operate.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first electrode 141 that can be located at or near its distal end, and a second electrode 142 that can be located at or near the electrode 141. The electrodes 141 and 142 can be electrically connected to the IMD 110 such as via separate conductors in the lead 108A, such as to allow for sensing of the right atrial activity and/or delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first electrode 152 that can be located at distal end, a second electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and/or delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IN/ID 110 such as via separate conductors in the lead 108C such as to allow for sensing the LV electrogram and/or delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible. For example, the it is contemplated that the cardiac system could be a subcutaneous implantable cardioverter defibrillator (S-ICD) including subcutaneously positioned electrodes, or the cardiac system could include one or more leadless pacemakers placed directly in or on the heart.

As illustrated, the CRM system 100 can include a selective cardiac stimulation circuit 113. The selective cardiac stimulation circuit 113 can be configured to detect at least one physiologic signal at two or more candidate stimulation sites at or within at least one chamber of the heart 105, such as the left ventricle (LV) 134. The physiologic signal can include cardiac electrical signals or cardiac mechanical signals. The physiologic signal can be an intrinsic cardiac signal or an evoked physiologic response such as in response to electrostimulation via one or more of the electrodes 161-164 on the lead 108C. The selective cardiac stimulation circuit 113 can determine, for the two or more candidate stimulation sites, an activation timing indicator using the physiologic signal at the corresponding candidate stimulation site. The selective cardiac stimulation circuit 113 can also detect, for the two or more candidate stimulation sites, a myocardial infarction (MI) indicator that indicates presence of, or relative spatial proximity or remoteness of the corresponding candidate stimulation sties, to a MI tissue. The MI indicator can be detected using the detected physiologic signal. The selective cardiac stimulation circuit 113 can perform a comparison of the activation timing indicators associated with the two or more candidate stimulation sites, and a comparison of the MI indicators associated with the two or more candidate stimulation sites. Based on the comparisons, the selective cardiac stimulation circuit 113 can select, automatically or based on a user input, at least one target stimulation site from the two or more candidate stimulation sites and/or the selective cardiac stimulation circuit 113 can generate a presentation for display in a user interface, including a display of information such as the two or more candidate stimulation sites with at least some of the respective MI indicators for selection of the at least one target stimulation site, or an indication of the selected at least one target stimulation site. The selective cardiac stimulation circuit 113 can additionally generate one or more second indicators indicative of therapy efficacy, battery longevity, or complication of stimulation. The selective cardiac stimulation circuit 113 can generate a selectable set of candidate electrostimulation vectors including electrodes positioned at the at least one target stimulation site. The users may rank at least some of the candidate electrostimulation vectors according to an order of the MI indicators or the one or more second indicators. The selective cardiac stimulation circuit 113 can be programmed, automatically or based on a user input, to deliver therapeutic electrostimulation to the selected target stimulation sites. Examples of the selective cardiac stimulation circuit are described below, such as with reference to FIGS. 2-3 and 6.

In an example, the selective cardiac stimulation circuit 113 can be implemented in a cardiac mapping system configured to provide information about spatial distribution of cardiac potentials in at least a portion of a heart, such as a heart chamber. In lieu of analyzing a plurality of candidate stimulation sites and comparing the corresponding activation timing indications and the corresponding MI indicators, the selective cardiac stimulation circuit 113 can start from a candidate stimulation site, detect a corresponding activation timing indicator and a corresponding myocardial infarction (MI) indicator indicative of presence of, or relative spatial proximity or remoteness of the corresponding candidate stimulation sties, to a MI tissue. The selective cardiac stimulation circuit 113 can use the activation timing indicator and the MI indicator, each associated with the candidate stimulation site under analysis, to create a representation in the cardiac potential map at the corresponding candidate stimulation site. If the activation timing indicator and the MI indicator meet respectively specified criterion (such as the activation timing is above an activation timing threshold and the cardiac electrical signal detected at the candidate stimulation site exceeds a specified amplitude threshold), the selective cardiac stimulation circuit 113 can deem the candidate stimulation site as a target stimulation site. If the activation timing indicator and the MI indicator do not meet respectively specified criterion, then the selective cardiac stimulation circuit 113 can test another candidate stimulation site different from the previously analyzed candidate site. The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The selective cardiac stimulation circuit 113 can be implemented at the external system 120 such as using data extracted from the IMD 110 or data stored in a memory within the external system 120. Portions of the selective cardiac stimulation circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
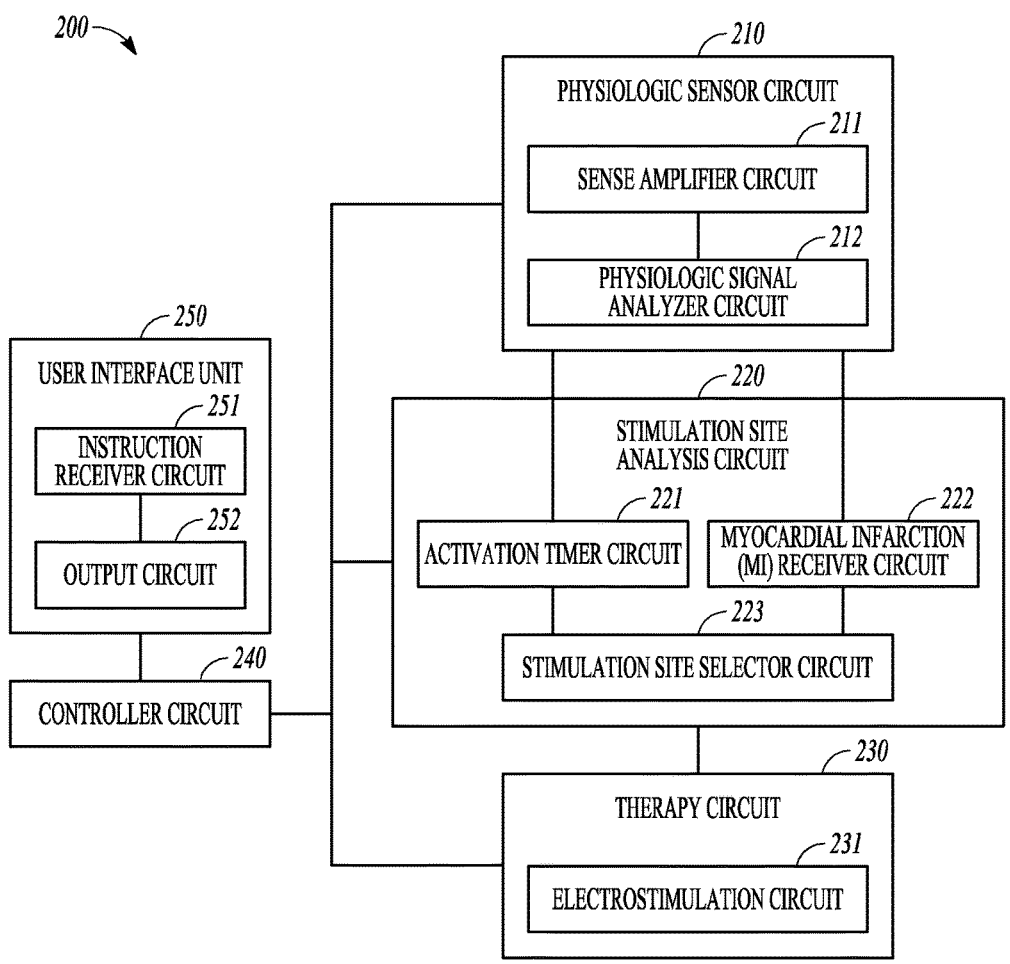
FIG. 2 illustrates generally an example of a selective electrostimulation circuit.

FIG. 2 illustrates generally an example of a selective electrostimulation circuit 200, which can be an embodiment of the selective cardiac stimulation circuit 113, as shown in FIG. 1. The selective electrostimulation circuit 200 can include one or more of a physiologic sensor circuit 210, a stimulation site analysis circuit 220, a controller circuit 240, and a user interface unit 250. The selective electrostimulation circuit 200 can additionally include an optional therapy circuit 230.

The physiologic sensor circuit 210 can include a sense amplifier circuit 211 and a physiologic signal analyzer circuit 212. The sense amplifier circuit 211 can sense a physiologic signal and perform signal amplification, digitization, filtering, or other signal conditioning operations. In an example, the physiologic signal can be sensed under a specified condition, such as when the heart undergoes an intrinsic rhythm, such as a sinus rhythm, or when the heart is stimulated in accordance with a specified stimulation protocol. Examples of the physiologic signals can include cardiac electrical signals such as electrocardiograms (ECGs) such as sensed by using electrodes non-invasively attached to the body surface, subcutaneous ECGs such as sensed by using subcutaneously placed electrodes, or intracardiac electrograms (EGMs) such as sensed by using electrodes on one or more of the leads 108A-C or the can 112 or sensed by electrodes disposed in the thoracic cavity. The physiologic signals can additionally or alternatively include signals indicative of cardiac mechanical activities (hereinafter "cardiac mechanical signals") such as contractions of an atrium or a ventricle as a response to an intrinsic heart rhythm or a stimulation of the heart. The cardiac mechanical signals can be sensed from an ambulatory accelerometer or a microphone configured to sense the heart sounds in a patient, from an impedance sensor configured to sense cardiac or thoracic impedance change as a result of cyclic cardiac contractions, or from a pressure sensor configured to sense blood pressure signals, among other sensors for sensing cardiac mechanical signals.

The physiologic signal analyzer circuit 212 can detect one or more characteristic signal features from the cardiac electrical signal or cardiac mechanical signal. The characteristic signal features can include temporal or morphological features indicative of intrinsic cardiac activity such as a P wave, Q wave, R wave, QRS complex, or T wave that can be detected from a surface ECG, a subcutaneous ECG, or an intracardiac EGM. The characteristic signal features can also be indicative of evoked cardiac activity such as evoked electrical or mechanical activation in response to an electrostimulation of the heart. The physiologic signal analyzer circuit 212 can detect the characteristic signal features by comparing an intensity measure of the physiologic signal to a threshold. A signal feature is deemed detected if the intensity measure exceeds the threshold or beyond a specified margin. Examples of the intensity measure can include signal amplitude, slope or rate of change of signal amplitude, amplitude of a transformed physiologic signal such as integrated signal, or a frequency-domain measurement such as power spectral density.

The physiologic sensor circuit 210 can sense and analyze two or more physiologic signals simultaneously or sequentially. The two or more physiologic signals can be sensed respectively from two or more sites at or within a heart chamber, such as a left ventricle (LV), a right ventricle (RV), a left atrium (LA), or a right atrium (RA) of the heart. The physiologic sensor circuit 210 can sense two or more physiologic signals via respective sensing vectors that include respective electrodes removably positioned at or within a chamber of the heart. For example, the physiologic sensor circuit 210 can sense two or more physiologic signals from two or more LV sites using respective sensing vectors each including at least one of electrodes 161-164 on the LV lead 133. An example of the LV sensing vector can include a bipolar sensing vector such as between a pair of electrodes selected among 161-164, or between one of the electrodes 161-164 and another electrode positioned on a different chamber or attached to a different lead (such as one of electrodes 152-155 on the RV lead 108B, or electrodes 141 or 142 on the RA lead 108A). Another example of the LV sensing vector can include a unipolar sensing vector such as between one of the electrodes 161-164 and the can 112.

The stimulation site analysis circuit 220 can be coupled to, or in communication with, the physiologic sensor circuit 210, and configured to determine one or more target stimulation sites in a chamber such as left ventricle (LV) of the heart such as by using the physiologic signal sensed by the physiologic sensor circuit 210. In an example, the stimulation site analysis circuit 220 can be implemented as a part of a microprocessor circuit within the selective electrostimulation circuit 200. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein.

In an example, the stimulation site analysis circuit 220 can include circuit sets comprising one or more other circuits or sub-circuits, that may, alone or in combination, perform the functions, methods, or techniques described herein. In an example, hardware of the circuit set may be immutably designed to carry out a specific operation (e.g., hardwired).

In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the stimulation site analysis circuit 220 can include one or more of an activation timer circuit 221, a myocardial infarction (MI) receiver circuit 222, and a stimulation site selector circuit 223. The activation timer circuit 221, coupled to the physiologic sensor circuit 210, can be configured to determine respective activation timing indicators using the respective physiologic signals such as sensed by the physiologic sensor circuit 210. The activation timing indicators are associated with the corresponding two or more candidate stimulate sites at or within the at least one chamber of a heart. The activation timing indicators can be computed as a time interval between a characteristic signal feature and a reference time. Examples of the characteristic signal feature can include an intrinsic or evoked cardiac electrical depolarization or a mechanical activation. Examples of the activation timer circuit 221 are described below, such as with reference to FIG. 3.

The MI receiver circuit 222 can receive respective MI indicators corresponding to the two or more candidate stimulation sites. In an example, the respective MI indicators can be pre-determined and stored in memory accessible by the MI receiver circuit 222. In an example, the MI receiver circuit 222 can include a MI detector circuit coupled to the physiologic sensor circuit 210, and detect the respective MI indicators for the two or more candidate stimulation sites using cardiac electrical signals sensed at the two or more candidate stimulation sites. The MI indicators can be indicative of presence of, or relative spatial proximity of each of the two or more candidate stimulation sites to, a MI tissue. Examples of the MI receiver circuit 222 are described below, such as with reference to FIG. 3.

The stimulation site selector circuit 223 can be communicatively coupled to the activation timer circuit 221 and the MI receiver circuit 222, and configured to select, automatically or based on a user input, at least one target stimulation site from the two or more candidate stimulation sites using the respective activation timing indicators and the respective MI indicators. The stimulation site selector circuit 223 can include a first comparator circuit that can compare the activation timing indicators associated with the two or more candidate stimulation sites. The stimulation site selector circuit 223 can include a second comparator circuit that can compare the MI indicators associated with the two or more candidate stimulation sites. By using one or both of the comparison among the activation timing indicators and the comparison among the MI indicators, the stimulation site selector circuit 223 can select, automatically or based on a user input, at least one target stimulation site that corresponds to the latest activation timing indicator among the two or more candidate stimulation sites and a MI indicator indicating the corresponding target stimulation site being outside of or remote to a MI tissue. A selected site can be determined further in response to the latest activation timing indicator exceeding a threshold or falling within a specified range. Examples of the stimulation site selector circuit 223 are discussed below, such as with reference to FIG. 3.

In an example, the stimulation site selector circuit 223 can select at least two target stimulation sites from the two more candidate stimulations sites. The selection of the at least two target stimulation sites can be performed in a sequential process, such that a first target site, SP1, is selected first, and SP1 is used in the subsequent process of determining a different second target sites SP2. In an example, a first set of physiologic signals can be sensed from multiple candidate sites on a chamber such as a LV of the heart when the heart undergoes a specified intrinsic rhythm such as sinus rhythm or when the heart is stimulated according to a specified stimulation protocol such as RA pacing. The activation timer circuit 221 can determine a first set of activation timing indicators associated with the multiple candidate sites using the first set of physiologic signals. The first set of activation timing indicators can each be computed as time intervals between the detected characteristic signal feature and a Q wave or timing of a stimulation artifact of the RA pacing. The MI receiver circuit 222 can determine a first set of activation timing indicators and a first set of MI indicators associated with the multiple candidate sites using the first set of physiologic signals. The stimulation site selector circuit 223 can use the first set of activation timing indicators and the first set of MI indicators to determine first target site SP1 which, for example, has a corresponding activation timing indicator later than other of the first set of activation timing indicators, and a corresponding MI indicator indicating the site SP1 being outside of or remote to a MI tissue. Then, a second set of physiologic signals can be sensed when the heart is stimulated according to a specified stimulation protocol such as electrostimulation of at least the first target site SP1 that has previously been determined. The activation timer circuit 221 and the MI receiver circuit 222 can respectively determine a second set of activation timing indicators and a second set of MI indicators using the second set of physiologic signals sensed from the multiple sites, excluding the pre-selected first target site SP1, on the chamber such as the LV of the heart. The second activation timing indicators can each be computed as a time interval between the detected characteristic signal feature and the electrostimulation at the first selected site SP1. The stimulation site selector circuit 223 can use the second set of activation timing indicators and the second set of MI indicators to determine the second target site SP2 out of the multiple sites excluding the pre-selected first target site SP1. The criteria for selecting SP2, as applied to the activation timing indicators and the MI indicators, can be similar to the criteria for selecting SP1. This process of sequential selection of targeting stimulations sites can be repeated, such as to determine a third (SP3) or additional target stimulation sites, which is considered to be within the contemplation of the present invention.

The selective electrostimulation circuit 200 can include an optional therapy circuit 230 configured to deliver a therapy to the patient using the selected at least one target stimulation site. In an example, the therapy can be delivered based on information including the activation timing indicators and the MI indicators at the two or more candidate stimulation sites. The therapy circuit 200 can include an electrostimulation circuit 231 that can deliver cardiac stimulation, neural stimulation, cardioversion, defibrillation, or other types of electrical therapies. In an example, the electrostimulation circuit 231 can be coupled to at least one stimulation electrode positioned at the selected at least one target stimulation site to deliver electrostimulation at the target stimulation sites. The electrostimulation, such as a pulse train, can be produced by the IMD 100 or an external pulse generator, and delivered to the two or more candidate stimulation sites of the heart via a pacing delivery system such as one or more of the leads 108A-C and the respectively attached electrodes. The electrostimulation can be delivered between an anode and a cathode. The anode and the cathode form a pacing vector. The electrostimulation can include a unipolar or a bipolar pacing configuration. The unipolar pacing can involve stimulation between an electrode positioned at or near a target stimulation site of the heart (such as an electrode on one of the leads 108A-C), and a return electrode such as the IMD can 112. The bipolar pacing can involve stimulation between two electrodes on one or more of the leads 108A-C.

The electrostimulation circuit 231 can deliver single site stimulation or multisite stimulation. In an example, only one target site SP1 is selected, and the electrostimulation circuit 231 can deliver single site electrostimulation using at least an electrode positioned at SP1. In another example, at least two target sites, SP1 and SP2, are selected, and the electrostimulation circuit 231 can deliver multisite stimulation including electrostimulation at both SP1 and SP2. The multisite stimulation can be delivered at multiple sites within the same cardiac cycle, either simultaneously or separated by a specified temporal offset less than a sensed or paced time interval value of the cardiac cycle. As an example, the temporal offset can be between 0-100 msec. In an example, the electrostimulation circuit 231 can program and deliver a first electrostimulation to SP1 and a different second electrostimulation to SP2, where the second electrostimulation differs from the first electrostimulation by at least one stimulation parameter including an amplitude, a pulse width, a duty cycle, a duration, or a frequency.

For multisite stimulation, the two or more sites for electrostimulation can include anatomical regions inside, or on an epicardial surface of, one or more heart chambers, including right atrium (RA), right ventricle (RV), left atrium (LA), and left ventricle (LV), or tissues surrounding any of the chambers. In an example, the electrostimulation circuit 231 can deliver electrostimulation to at least a site at RV and a site at LV. In another example, the multisite stimulation circuit 212 can deliver electrostimulation to two or more sites at the same chamber, such as two or more sites in LV which is hereinafter referred to as "multisite LV pacing." The multisite LV pacing can be achieved using two or more LV pacing vectors. Each LV pacing vector includes at least one of an anode or a cathode selected from LV electrodes distributed in one or more LV leads, catheters, or non-tethered pacing units, such as electrodes 161-164 on the LV lead 133. The electrostimulation circuit 231 can deliver multisite LV pacing using one or more of a bipolar pacing between two LV electrodes, a bipolar pacing between an LV electrode and a RV or RA electrode, a tripolar pacing between one or more LV electrodes and a RV or RA electrode, or a unipolar pacing between an LV electrode and the IMD can 112. The electrostimulation can be delivered to the two or more sites within a cardiac cycle, such as simultaneous stimulation or asynchronous stimulation separated by a specified temporal offset less than a sensed or paced time interval value of the cardiac cycle.

The controller circuit 240 can receive external programming input, such as from an instruction receiver circuit 251, to control the operations of the physiologic sensor circuit 210, the stimulation site analysis circuit 220, the optional therapy circuit 230, and the data flow and instructions between these components and respective subcomponents. In an example, the controller circuit 240 can control the physiologic sensor circuit 210 to sense of the physiologic signals at each of the two or more candidate stimulation sites. The controller circuit 240 can schedule the activation timer circuit 221 and the MI receiver circuit 222 to respectively produce the activation timing indicators and the MI indicators for the candidate stimulation sites. In an example, the controller circuit 240 can schedule a sequential process of generating the activation timing indicators and the MI indicators for the candidate stimulation sites, such as during multiple test sessions each used for determining the activation timing indicator and the MI indicator associated with a particular candidate stimulation site. In another example, the controller circuit 240 can schedule a parallel process of generating the activation timing indicators and the MI indicators for the candidate stimulation sites, such as determining the activation timing indicators and the MI indicators associated with all the candidate stimulation sites within the same cardiac cycle or the same test session.

The user interface unit 250 can include an instruction receiver circuit 251 and an output circuit 252. The instruction receiver circuit 251 can receive user's input including programming options or parameter values for physiologic signal sensing, calculation of activation timing, determination of MI indicators, or the parameters of the therapies for delivery at the selected target stimulation sites. The instruction receive circuit 251 can include an input device enabling the system user to make programming options, such as a keyboard, on-screen keyboard, mouse, trackball, touchpad, touch-screen, or other pointing or navigating devices. The instruction receiver circuit 251 can receive user's selection of at least one target stimulation site from the candidate sites, or a user's instruction that confirms, deselects, overrides, or otherwise modifies the selected at least one target stimulation site selected by the stimulation site selector circuit 223.

The output circuit 252 can produce a human-perceptible presentation, such as on a display, of information including an indication of the selected at least one target stimulation site. The output circuit 252 can additionally or alternatively presents on a display the activation timing indicators and the MI indicators associated with at least a part of the candidate stimulation sites, such that the system user can select from the candidate stimulation sites at least one target stimulation site. The information can be presented in a table, a chart, a diagram, or any other types of textual, tabular, or graphical presentation format. The presentation of the output information can include audio or other media format to alert the system user of the stimulation sites being selected or not selected. In an example, at least a portion of the user interface unit 250, such as the display, can be implemented in the external system 120.

In an example, the selective electrostimulation circuit 200 can include a stimulation vector selector circuit in addition to, or in lieu of, the stimulation site analysis circuit 220. The stimulation vector selector circuit can be configured to select one or more stimulation vectors from a plurality of candidate stimulation vectors. Each stimulation vector can include an anode and a cathode electrode. In an example, the cathode or the anode can include an electrode positioned at a selected site at a heart chamber (such as the LV). In an example, the stimulation vector selector circuit can select the one or more selected stimulation vectors that respectively include a cathode positioned at the selected stimulation sites corresponding to latest activation timing indicator, such as determined by the stimulation site analysis circuit 220. In an example, the stimulation vector selector circuit can use the activation timing indicator and one or more additional parameters to determine the one or more selected stimulation vectors. Examples of the additional parameters can include lead impedance as sensed between the stimulation electrodes, pacing threshold indicative of minimal energy required to capture the cardiac tissue, absence of or significance of phrenic nerve stimulation during stimulation, power consumption by stimulation and impact on longevity of the pulse generator, among others. The electrostimulation circuit 231 can deliver multisite electrostimulation according to the selected one or more stimulation vectors.

Figure 3:
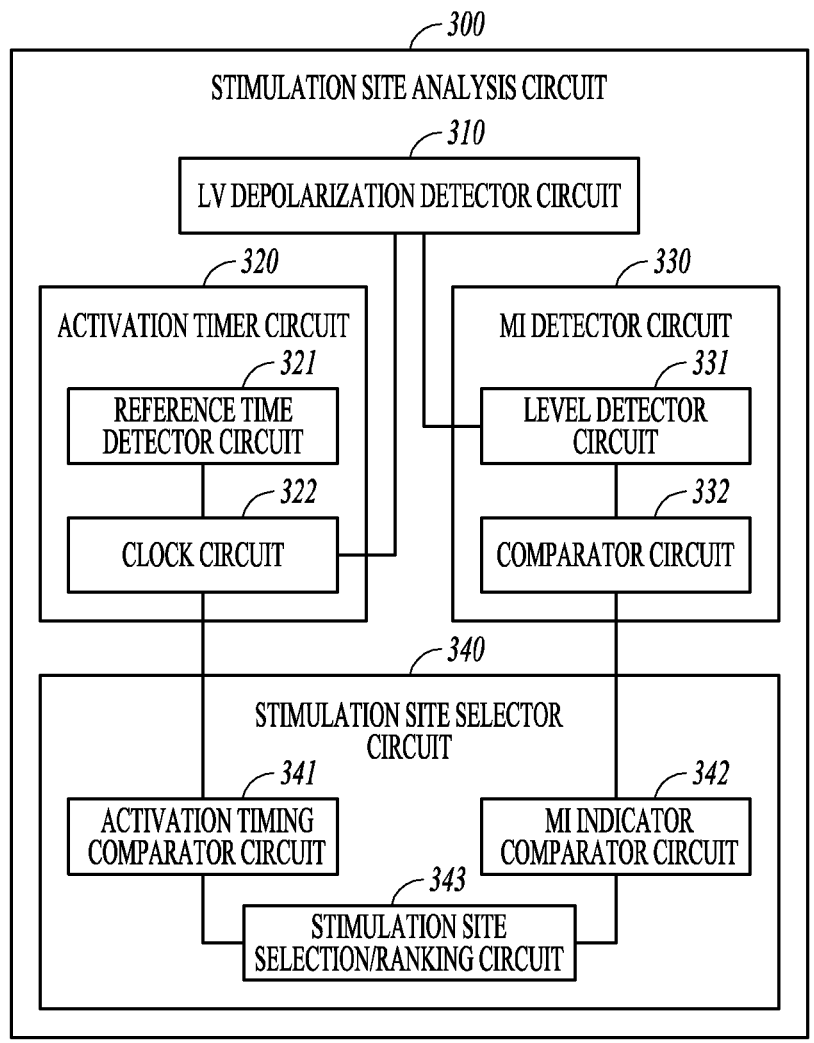
FIG. 3 illustrates generally an example of a stimulation site analysis circuit.

FIG. 3 illustrates generally an example of a stimulation site analysis circuit 300, which can be an embodiment of the stimulation site analysis circuit 220 in FIG. 2. The stimulation site analysis circuit 300 can be configured to select at least one LV target site from two or more candidate sites at or within the LV of the heart. The stimulation site analysis circuit 300 can include an LV depolarization detector circuit 310, an activation timer circuit 320 which can be an embodiment of the activation timer circuit 221, a MI detector circuit 330 which can be an embodiment of the MI receiver circuit 222, and a stimulation site selector circuit 340 which can be an embodiment of the stimulation site selector circuit 223. As an alternative to LV target stimulation site selection, the stimulation site analysis circuit 300 can be modified and configured to select target stimulation site at or within a different chamber of the heart, such as RV, RA, or LA, which is within the contemplation of the present invention.

The LV depolarization detector circuit 310 can be configured to detect depolarizations from the cardiac electrical signals sensed by the physiologic sensor circuit 210. The cardiac electrical signals can be sensed at two or more candidate sites of the LV of heart, such as multiple sites on the LV epicardial surface, LV endocardial surface, or within the LV myocardium. The cardiac electrical signals can include electrogram (EGM) sensed via sensing electrodes removably positioned at the two or more LV candidate sites, such as among the electrodes 161-164 on the LV lead 108C. The EGM can indicate depolarization of the tissue at or around the corresponding LV candidate site. In an example, the cardiac electrical signals are intrinsic LV EGM, and the LV depolarization detector circuit 310 can detect intrinsic depolarizations at the two or more LV candidate sites. In another example, the cardiac electrical signals can include evoked LV EGM indicative of evoked response to an extrinsic stimulation of a portion of the heart, such as stimulation of one of a right ventricle (RV), a right atrium (RA), or a left ventricle (LV) of the heart. The intrinsic or the evoked depolarization can be characterized by elevated voltage or distinct morphology. The LV depolarization detector circuit 310 can include a comparator circuit that can compare the amplitude of the EGM, or the amplitude of a rectified or integrated EGM, to a threshold. The LV depolarization detector circuit 310 can detect the intrinsic or the evoked LV depolarization if the amplitude exceeds a threshold. In some cases, the LV depolarization detector circuit 310 can detect the intrinsic or the evoked LV depolarization if a rate of change of the EGM amplitude exceeds a threshold, or if a morphology of the EGM matches within a specified degree a representative template of the LV depolarization.

The activation timer circuit 320 can include a reference time detector circuit 321 and a clock circuit 322. The reference time detector circuit 321 can determine a reference time, such as timing of a Q wave of an intrinsic QRS complex, timing of intrinsic activation at the RV or RA, or timing of the stimulation of a portion of the heart that produces the evoked responses at the LV candidate sites, such as timing of a pacing artifact of RA pacing, or timing of a pacing artifact of RV pacing. The clock circuit 322 can measure timing of a characteristic feature (e.g., a peak) of the detected LV depolarizations, and produce the activation timing indicator as a time interval between the timing of the detected LV depolarizations and the reference time, such as Q-LV intervals, RV-LV intervals, or RA-LV intervals, among others.

The MI detector circuit 330 can include a level detector circuit 331 and a comparator circuit 332. The level detector circuit 331 can measure intensity, such as amplitude, of the detected LV depolarizations at the two or more LV candidate stimulation sites. The present inventors have recognized that the LV intensity, such as the amplitude of the LV EGM, can be substantially reduced if the LV EGM is sensed at a site that is within or in close proximity to one of a MI tissue, a scar or fibrous tissue, a tissue of prolonged ischemia, or any other tissue with pathologically slow electrical conductivity or functional block. The present inventors have also recognized that the EGM sensed at these sites may also demonstrate late activation such as compared to other sites that are relatively more remote to a MI tissue. As such, although stimulation at a site of late activation may recruit more viable cardiac tissue and thus may offer better therapeutic outcome, stimulation at a site within or in proximity to the MI tissue may lead to worse therapeutic outcome than stimulation at a site remote to, or absent of, the MI tissue.

The comparator circuit 332 can compare the intensity of the detected LV depolarization to a specified criterion. In an example, the comparator circuit 332 can compare the amplitudes of the cardiac electrical signals to a threshold. Based on the comparison, the MI detector circuit 330 can detect, for each of the two or more LV candidate sites, a respective MI indicator as one of a first indicator of being spatially proximal to a MI tissue if the determined amplitude falls below a threshold, or a second indicator of being spatially remote to, or absence of, a MI tissue if the determined amplitude exceeds the threshold. In an example, the MI indicator can have a numerical value representing the likelihood of the corresponding candidate stimulation site being within or in close proximity to one of a MI tissue, a scar or fibrous tissue, a tissue of prolonged ischemia, or any other tissue with pathologically slow electrical conductivity or functional block. The MI indicators can alternatively have a categorical value, such as an indication of "presence" or "absence" of a MI tissue, or being "proximal" or "remote" to a MI tissue, or any intermediate categories between "proximal" or "remote" to a MI tissue.

The stimulation site selector circuit 340 can include an activation timing comparator 341 coupled to the activation timer circuit 320, a MI comparator circuit 342 coupled to the MI detector circuit 330, and a stimulation site selector 343. The activation timing comparator 341 can compare the LV depolarization timings, such as the time intervals with respect the reference time, of the two or more LV candidate stimulation sites, and identify one or more sites, out of the candidate sites, that have the corresponding LV activation timings later in time than other of the candidate sites. The MI indicator comparator circuit 342 can compare the MI indicators of the two or more LV candidate stimulation sites, and identify one or more sites, out of the candidate sites, that have the corresponding MI indicators indicating the identified one or more sites being spatially remote to a MI tissue. In an example, the MI indicator comparator circuit 342 can identify such "MI-remote" sites by comparing the LV intensity to a specified criterion, such as when the LV intensity exceeds a threshold.

The stimulation site selection/ranking circuit 343 can use the comparison of the activation timing and the comparison of the MI indicators to select at least one LV target stimulation site from the two or more candidate sites. In an example, the stimulation site selection/ranking circuit 343 can select the at least one target stimulation site associated with respective activation timing indicators indicating the at least one target stimulation site activating later than other of the two or more candidate stimulation sites, and respective MI indicators indicating the at least one target stimulation site being spatially remote to a MI tissue.

In an example, the stimulation site selection/ranking circuit 343 can be configured to produce a rankable set of a part or all of the candidate stimulation sites using the respective activation timing indicators and the respective MI indicators. Each candidate stimulation site of the rankable set is associated with the corresponding activation timing indications such as the time intervals with respect to a reference time, and the corresponding MI indicators such as amplitude or intensity measure of LV depolarization. The rankable set can be displayed in a user interface unit 250, and the system user can rank the candidate stimulation sites in the rankable set according to one or both of the activation timing indications and the MI indicators.

In an example, the stimulation site selection/ranking circuit 343 can be configured to automatically rank a part or all of the candidate stimulation sites using the respective activation timing indicators and the respective MI indicators. For example, the stimulation site selection/ranking circuit 343 can rank the candidate stimulation sites according to a descending order of the activation timings, such that the candidate stimulation sites with a later activation timing or a longer interval from the reference time, is ranked at a higher priority than the candidates stimulation sites with an earlier activation timing or a shorter interval from the reference time. The stimulation site selection/ranking circuit 343 can alternatively rank the candidate stimulation sites according to a descending order of the MI indicators, such that the candidate stimulation sites having an indication of being more remote to a MI tissue, or having a larger amplitude of LV depolarization, is ranked at a higher priority than the candidates stimulation sites having an indication of being more proximal to a MI tissue, or having a smaller amplitude of LV depolarization.

Figure 4:
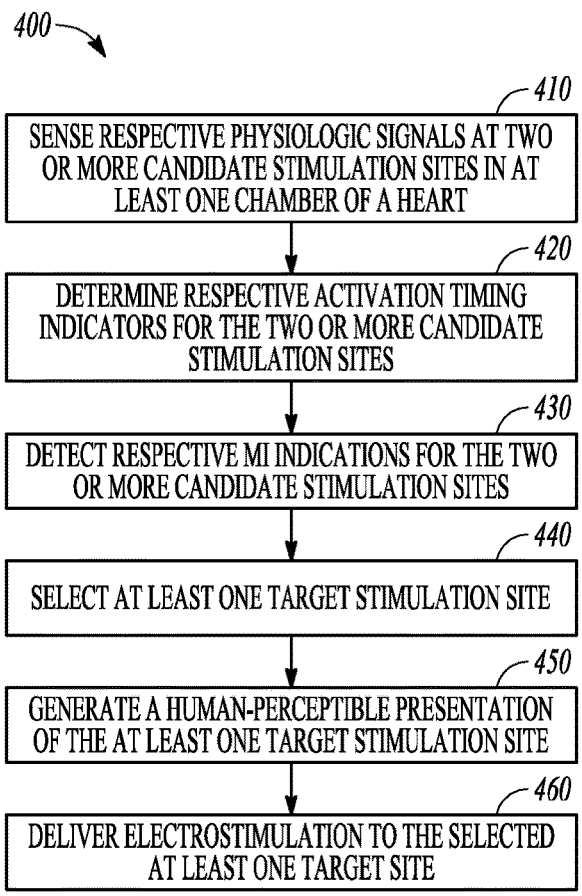
FIG. 4 illustrates generally an example of a method for selecting one or more stimulation sites at or within a heart of a subject.

FIG. 4 illustrates generally an example of a method 400 for selecting one or more stimulation sites at or within a heart of a subject. The method 400 can be implemented and operate in an implantable, wearable, or other ambulatory medical device, or in a remote patient management system. In an example, the method 400 can be performed by the selective electrostimulation circuit 200 or any modification thereof.

The method 400 can begin at step 410, where respective physiologic signals can be sensed at two or more candidate stimulation sites in at least one chamber of the heart, such as a left ventricle (LV). The physiologic signals can be sensed under a specified condition, such as when the heart undergoes an intrinsic rhythm such as a sinus rhythm, or when the heart is stimulated such as during pacing at a right atrium (RA) or a right ventricle (RV). The physiologic signal can include cardiac electrical signals such as intracardiac electrograms (EGMs) sensed at one or more cardiac sites, such as by using electrodes on one or more of the leads 108A-C or the can 112. Additionally or alternatively, the physiologic signals can include cardiac mechanical signals, such as heart sounds signals, blood pressure signals, or other signals indicative of contractions of an atrium or a ventricle as a response to an intrinsic heart rhythm or a stimulation of the heart.

At 420, respective activation timing indicators associated with the two or more candidate stimulation sites can be determined using the sensed physiologic signals. In an example, the activation timing indicators can include relative timing of a characteristic signal feature of the physiologic signals respectively sensed at the two or more candidate stimulation sites. Examples of the characteristic signal features can include peak of the LV EGM within a cardiac cycle, temporal or morphological signal features indicative of intrinsic cardiac activity such as a P wave, Q wave, R wave, QRS complex, or T wave that can be detected from a surface ECG a subcutaneous ECG; or an intracardiac EGM, or evoked cardiac activity such as evoked electrical or mechanical activation in response to an electrostimulation of the heart. In another example, the activation timing indicators can be computed as a time interval between a characteristic signal feature of the physiologic signal and a reference time. Examples of the reference time can include timing of a Q wave of an intrinsic QRS complex, timing of intrinsic activation at the RV or RA, timing of the stimulation of a portion of the heart such as timing of a pacing artifact of RA pacing, or timing of a pacing artifact of RV pacing.

At 430, respective MI indicators at the two or more candidate stimulation sites can be detected using the physiologic signals sensed at the two or more candidate stimulation sites. The MI indicator can have a numerical or a categorical value. In an example, amplitude or other intensity metrics of the cardiac electrical signals sensed at the two or more candidate stimulation sites can be used to predict presence of, or relative spatial proximity of each of the two or more candidate stimulation sites to, a MI tissue, a scar or fibrous tissue, a tissue of prolonged ischemia, or any other tissue with pathologically slow electrical conductivity or functional block. Examples of generating the MI indicators are described below, such as with reference to FIG. 5.

At 440, at least one target stimulation site can be selected from the two or more candidate stimulation sites using the respective activation timing indicators and the respective MI indicators. In an example, the activation timing indicators associated with the two or more candidate stimulation sites are compared with each other, and the MI indicators associated with the two or more candidate stimulation sites are compared with each other. At least one target stimulation site can be selected if it has (1) a corresponding activation timing indicator later than other of the two or more candidate stimulation sites and (2) a corresponding MI indicator indicating the corresponding target stimulation site being outside of or remote to a MI tissue. The selected site can be further confirmed if the latest activation timing indicator exceeds a threshold or falls within a specified range.

At 450, a human-perceptible presentation of the two or more candidate stimulation sites with at least some of the respective MI indicators for selection of the at least one target stimulation site, or an indication of the at least one target stimulation site can be generated. The presentation can also include activation timing indicators and the MI indicators associated with the at least one target stimulation site. In an example, the presentation can include a part or all of the candidate stimulation sites, along with the respective activation timing indicators and the MI indicators, such that the system user can make the selection of at least one target stimulation site from the candidate stimulation sites. The information can be presented in a table, a chart, a diagram, or any other types of textual, tabular, or graphical presentation formats, for displaying to a system user. The presentation of the output information can include audio or other media format to alert the system user of the stimulation sites being selected or not selected.

The method 400 can include an optional step 460 of delivering electrostimulation at the selected at least one target site. The electrostimulation can be delivered between an anode and a cathode. The anode and the cathode form a pacing vector. The electrostimulation can include a unipolar or a bipolar pacing configuration. The stimulation can include single site stimulation if only one target site SP1 is selected, or multisite stimulation if at least two target sites, SP1 and SP2, are selected. The multisite stimulation can include anatomical regions inside, or on an epicardial surface of, one or more heart chambers, including right atrium (RA), right ventricle (RV), left atrium (LA), and left ventricle (LV), or tissues surrounding any of the chambers. In an example, the multisite stimulation can involve a first stimulation site SP1at RV and a second stimulation site SP2 at LV. In another example, the target stimulation sites SP1 and SP2 are in the same chamber, such as the LV. The respective electrostimulation delivered at SP1 and SP2 can be within the same cardiac cycle, either simultaneously or separated by a specified temporal offset less than a sensed or paced time interval value of the cardiac cycle. In an example, the temporal offset can be between 0-100 msec. In an example, the electrostimulation delivered at SP1 can be different from the electrostimulation delivered at SP2, by at least one stimulation parameter such as an amplitude, a pulse width, a duty cycle, a duration, or a frequency.

In some examples, the method 400 can include additional operation of receiving hemodynamic response to the stimulation at the site that corresponds to the latest activation. The hemodynamic response can be used in addition to, or in lieu of, the criterion such as the latest activation timing indicator exceeding a threshold. For example, upon selecting the at least one target stimulation site at 440, a "confirmatory" electrostimulation can be delivered to the at least one target stimulation site, and a resulting hemodynamic response can be sensed, such as by using a hemodynamic sensor. The hemodynamic response can include arterial pressure, pulmonary artery pressure, left atrial pressure, RV pressure, LV coronary pressure; thoracic impedance or cardiac impedance, blood temperature, one or more heart sounds, blood oxygen saturation, central venous pH value, among others. The at least one target stimulation site can be confirmed when the hemodynamic response meets a specified criterion such as indicative of an improvement of hemodynamic outcome beyond a specified margin over the stimulation without involving SP2 (e.g., electrostimulation at SP1).

In some examples, the method 400 can include generating a selectable set of candidate electrostimulation vectors. The candidate electrostimulation vectors can include electrodes positioned at the candidate stimulation sites. The method 400 can include selecting, automatically or based on a user input, at least one target electrostimulation vector from the selectable set. The selection can be based on the respective MI indicators or the respective one or more second indicators indicative of therapy efficacy, battery longevity, or complication of the electrostimulation vector. The candidate electrostimulation vectors can be ranked, automatically or based on a user input, according to a specified order (e.g., ascending or descending order) of a specified indicator such as an MI indicator, therapy efficacy indicator, battery longevity indicator, or complication indicator. In an example, the ranking can be a multi-level ranking process, including generating first ranked vectors by ranking the candidate electrostimulation vectors according to a first specified order (e.g., ascending or descending order) of first specified indicators, and generating at least second ranked vectors by ranking at least a portion of the first ranked vectors according to a second specified order (e.g., ascending or descending order) of second specified indicators, the portion of the first ranked vectors having corresponding first indicators meeting a specified condition. The first specified indicators can be different from the second specified indicators, and the first and second specified indicators are each selected from MI indicators, therapy efficacy indicators, battery longevity indicators, or complication indicators. The ranked candidate electrostimulation vectors can be presented to a user, such as displayed in the user interface unit 250. In an example, electrostimulation therapy can be programmed according to the selected at least one target electrostimulation vector and delivered to the heart.

Figure 5:
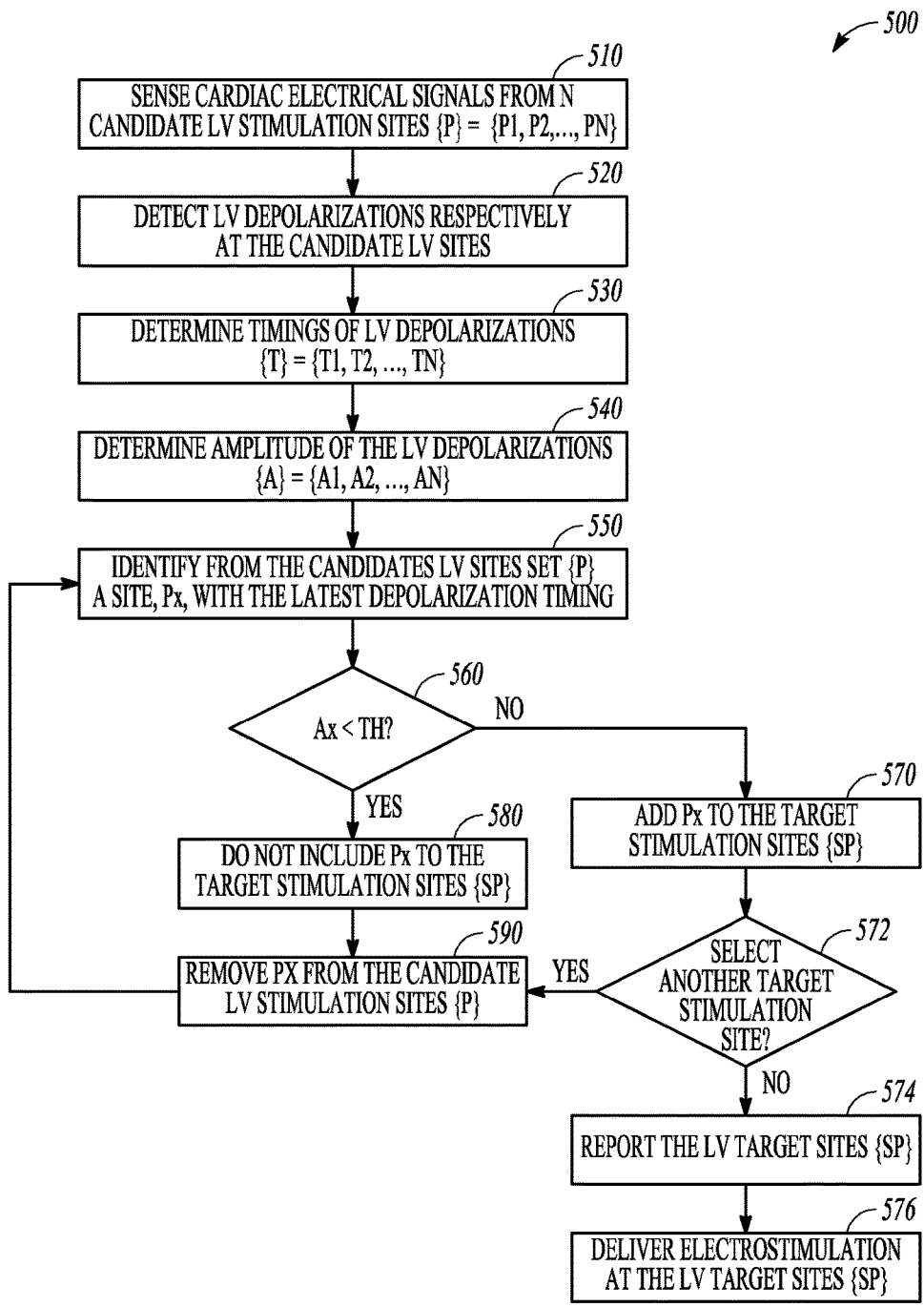
FIG. 5 illustrates generally an example of a method for selecting one or more stimulation sites in a heart for multisite left ventricle (LV) stimulation.

FIG. 5 illustrates generally an example of a method 500 for selecting one or more stimulation sites in a heart for multisite left ventricle (LV) stimulation. The method 500, which can be an embodiment of the method 400, can be performed by the selective electrostimulation circuit 200 or any modification thereof.

The method 500 begins at step 510 by sensing N cardiac electrical signals, denoted by $\{X\}=\{X1(t), X2(t), \ldots, XN(t)\}$, from N candidate LV stimulation sites $\{P\}=\{P1, P2, \ldots, PN\}$ on the surface or within the chamber of the LV. In an example, each cardiac electrical signals $Xi(t)$ can be sensed using a respective sensing vector comprising at least one LV sensing electrode placed at an LV stimulation site $Pi$. The N cardiac electrical signals can be sensed when the heart undergoes an intrinsic rhythm such as a sinus rhythm, or when electrostimulation is delivered to a portion of the heart, such as stimulation of one of a right ventricle (RV), a right atrium (RA), or a left ventricle (LV) of the heart.

At 520, depolarizations of LV can be detected from the cardiac electrical signals sensed from LV. In an example, depolarization at each candidate LV stimulation site $Pi$ can be detected if an amplitude of the LV EGM, or an amplitude of a rectified, integrated, or otherwise transformed LV EGM, exceeds a threshold. Alternatively, the depolarizations of LV can be detected if the rate of change of the EGM amplitude exceeds a threshold, or if the morphology of a portion of the LV EGM matches a representative template of the LV depolarization within a specified degree.

Timings and amplitudes of the detected LV depolarization can then be measured. At 530, timings of the detected LV depolarizations, denoted by $\{T\}=\{T1, T2, \ldots, TN\}$, can be detected. The LV timings $\{T\}$ can be measured as timings of characteristic features, such as peaks, of the detected LV depolarizations. In an example, the LV timings $\{T\}$ can be determined as time intervals between the timing of the detected LV depolarizations and a reference time. Examples of the reference time can include timing of a Q wave of an intrinsic QRS complex, timing of intrinsic activation at the RV or RA, or timing of the stimulation of a portion of the heart that produces the evoked responses at the LV candidate sites, such as timing of a pacing artifact of RA pacing, or timing of a pacing artifact of RV pacing. At 540, amplitude or other intensity metrics of the detected LV depolarizations, denoted by {A}={A1, A2, . . . , AN}, can be measured from the LV depolarizations.

At 550, a candidate site, denoted by Px, which has a corresponding activation timing later than other of the two or more candidate stimulation sites, can be identified. The present inventors have also recognized that electrostimulation at a site corresponding to later activation timing (than other stimulation sites) may result in better therapeutic outcome in some patients. However, the later activation timing may also occur at a site within or in proximity to a MI tissue, a scar or fibrous tissue, a tissue of prolonged ischemia, or any other tissue with pathologically slow electrical conductivity or functional block. To determine whether the identified site Px is within or in proximity to a MI tissue, the LV amplitude (or other intensity metrics) Ax of the LV depolarization at site Px can be compared to a threshold at 560. If the LV amplitude Ax falls below the threshold, then there is a high likelihood that the site Px is within or in close proximity to one of a MI tissue, a scar or fibrous tissue, a tissue of prolonged ischemia, or any other tissue with pathologically slow electrical conductivity or functional block. Therefore, at 580, the site Px is not included in the target stimulation sites {SP}. If the site Px is previously included in the target stimulation sites {SP}, it can be excluded or deselected from {SP}. At 590, the candidate LV stimulation sites {P} are updated by removing the site Px from {P}. The updated candidate LV stimulation sites {P} can then be used at 550 to identify another site with the latest depolarization timing.

If at 560 the LV amplitude Ax exceeds the threshold, then there is high likelihood that the site Px is outside of or remote to a MI tissue, a scar or fibrous tissue, a tissue of prolonged ischemia, or any other tissue with pathologically slow electrical conductivity or functional block. Therefore, at 570, the site Px can be added to the target stimulation sites {SP}. At 572, a decision is made as to whether selecting an additional target stimulation site, other than Px, for multisite LV stimulation. If an additional site is desired, then at 590 the candidate stimulation sites {P} can be updated by excluding Px from {P}, and the site selection process can be continued at 550. If no additional target stimulation site is desired at 572, selection process of the LV target sites {SP} can be completed, and the selected target sites {SP} can be reported to a system user at 574, such as by displaying in a user interface unit 250 information including an indication of the selected sites {SP}, along with the activation timing indicators and the MI indicators. At 576, electrostimulation can be delivered respectively at the LV target sites {SP}, such as single site LV stimulation at a single LV target site SP1, or multisite LV stimulation at two or more LV target sites.

Figure 6:
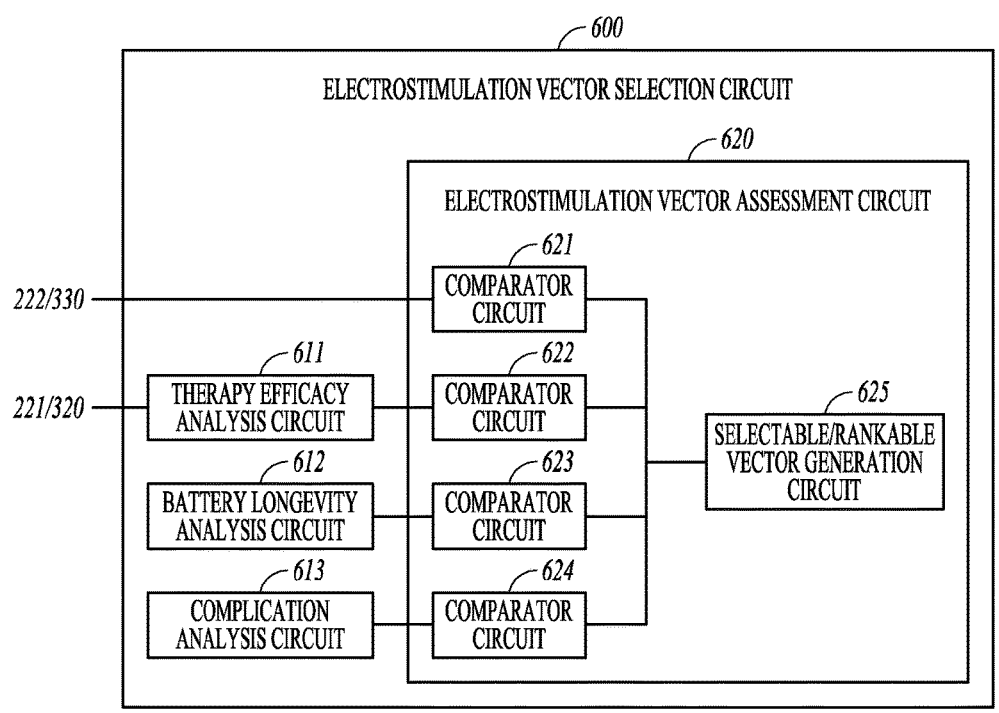
FIG. 6 illustrates generally an example of an electrostimulation vector selector circuit.

FIG. 6 illustrates generally an example of an electrostimulation vector selector circuit 600, which can be an embodiment of the stimulation site selector circuit 223 or the stimulation site selector circuit 340. The electrostimulation vector selector circuit 600 can include one or more of a therapy efficacy analysis circuit 611, a battery longevity analysis circuit 612, or a complication analysis circuit 613, and an electrostimulation vector assessment circuit 620.

The electrostimulation vector selector circuit 600 can receive an MI indicator from the MI receiver circuit 222 or the MI detector circuit 330. The MI indicator can indicate presence of, or relative spatial proximity of at least a portion of an electrostimulation vector, to a MI tissue. The therapy efficacy analysis circuit 611 can be configured to generate a therapy efficacy indicator indicating a therapeutic effect when the stimulation is delivered according to the electrostimulation vector, such as hemodynamic response to a cardiac resynchronization therapy (CRT) or multisite LV electrostimulation therapy. The therapy efficacy indicator can have a numerical value, where a larger value indicates a higher therapeutic efficacy. In another example, the therapy efficacy indicator has a descriptive categorical value selected from one or more of "very low", "low", "medium", "high", "very high", indicative of the level of therapeutic efficacy of the corresponding electrostimulation vector.

The therapy efficacy indicator can be generated using one or more electrical or mechanical signals such as produced by the physiologic sensor circuit 210. Electrical or mechanical signal metrics can be derived respectively from the electrical or mechanical signals, including: intensities (such as amplitudes) and timing of P wave, Q wave, R wave, QRS complex, or T wave detected from a surface ECG or a subcutaneous ECG; timing of sensed activation of at least a portion of a chamber of the heart such as RA, RV, and LV, obtained from the intracardiac EGMs; QRS width; electrical delay of a chamber of the heart such as LV electrical delay; interventricular conduction delay measured as the delay between LV activation to RV activation (LV-RV) delay; intraventricular delay; intensity of a component of the sensed HS signal including one or more of S1, S2, S3, or S4 heart sounds; mechanical delay such as time intervals indicative of systole or diastole; pressures inside a heart chamber; end-systolic volume; or end-diastolic volume; among others. In an example as illustrated in FIG. 6, the therapy efficacy analysis circuit 611 can generate the therapy efficacy indicator using the activation timings produced by the activation timer circuit 221 or the activation timer circuit 320.

The electrical or mechanical signal metrics can be predictive of patient hemodynamic response to the therapeutic cardiac electrostimulation. For example, the electrical delay can include a Q-LV interval measured from Q wave to left ventricle activation, measured from the onset of the intrinsic QRS (such as from the surface ECG) to local intrinsic activation at the LV stimulation site (such as detected as the first dominant peak on the LV electrogram). The Q-LV interval can be correlated with maximum rate of increase in LV pressure (LV dP/dt max), thus indicative of LV contractility. Q-LV interval therefore can be used to assess efficacy of the LV electrostimulation therapy delivered using a specified pacing vector. In another example, S1 intensity can be correlated with LV dP/dt max, thus indicative of the LV contractility. The mechanical delay can include left-ventricular ejection time (LVET), an interval from the opening to the closing of the aortic valve (mechanical systole). The LVET can be correlated with hemodynamic of the LV, and can be measured as an interval between S1 and S2 heart sound within the same cardiac cycle. S1 intensity and LVET therefore can both be used to assess efficacy of the LV electrostimulation therapy delivered using a specified pacing vector.

Additionally or alternative, the therapy efficacy indicator can be determined using a combination of at least some of the electrical signal metrics and at least some of the mechanical signal metrics. In one example, the therapy efficacy indicator can be determined based on analysis of the electromechanical coupling of the heart between a cardiac electrical signal and a cardiac mechanical signal, such as a cardiac timing interval (CTI). Examples of the CTI can include a pre-ejection period (PEP), a systolic timing interval (STI), or a diastolic timing interval (DTI), among others. In another example, the electrical signal metrics and the mechanical signal metrics are each assigned a score indicative of stimulation efficacy, and the therapy efficacy indicator can be determined as a collective presentation of the scores associated with the respective signal metrics. In another example, a composite score can be computed, such as using a linear or non-linear fusion algorithm, by combining the individual scores of the respective signal metrics. The composite score can be indicative of the therapeutic efficacy of the cardiac stimulation.

The battery longevity analysis circuit 612 can generate a battery longevity indicator corresponding to an electrostimulation vector. The battery longevity indicator can include projected remaining lifetime of the battery. The battery longevity indicator can have a numerical value or a categorical value. In an example, the battery longevity indicator has a numerical value of the projected remaining lifetime (e.g., years) of the battery. In another example, the therapy efficacy indicator has a categorical value of a range of remaining lifetime, such as one or more of "<1 year", "1-3 years", "3-5 years", ">5 years". The battery longevity indicator can include a relative longevity such as with respect to reference longevity. In an example, the reference longevity can be corresponding to the lifetime of the battery at its full capacity (e.g., a new battery before discharge), and the battery longevity indicator can indicate a fraction or percentage of the referenced longevity (e.g., ⅓, 25%, or half of full capacity). Battery longevity can be affected by a number of factors, including battery chemistry and battery voltage and impedance, configuration of electrostimulation vectors, polarity and number of electrodes that form an electrostimulation vector, lead impedance, capture threshold indicative of minimum amount of energy required to generating a propagating cardiac depolarization, mode or sequence of electrostimulation which determines the "ON" time for delivery of electrostimulation, stimulation parameters including pulse amplitude, pulse width, frequency, duty cycle, among others. In one example, the battery longevity can be estimated using a model of battery capacity and expected circuit performance, such as described by Russie, in U.S. Pat. No. 7,620,452, entitled "Systems and Methods for Managing the Longevity of an Implantable Medical Device Battery," which is herein incorporated by reference in its entirety. In another example, the longevity can be calculated based on sensed capacity as measured by a coulometer or a capacity-by-voltage device, such as described by Gandhi et al. in U.S. Pat. No. 8,055,343, entitled "Dynamic battery management in an implantable device," which is herein incorporated by reference in its entirety.

The complication analysis circuit 613 can generate a complication indicator indicating non-cardiac activation produced by an electrostimulation using the electrostimulation vector to the heart. The complications can include unintended nerve or skeletal muscle stimulation caused by excessive energy delivered to the heart such as due to a high capture threshold, or close proximity between the cardiac stimulation electrode and the nerves or the skeletal muscle, such as stimulation of skeletal muscle, diaphragm, phrenic nerve stimulation (PNS), unintended nerve stimulation, anodal cardiac stimulation, or any other parameters that do not support intended cardiac therapeutic effect. The complication analysis circuit 613 can be coupled to an accelerometer sensor configured to sense skeletal muscle activation in response to the cardiac electrostimulation delivered using an electrostimulation vector. Alternatively or additionally, the complication analysis circuit 613 can be coupled to a microphone sensor or an electromyogram (EMG) sensor to detect an activation of the laryngeal muscles, such as coughing response to undesirable activation of the laryngeal muscles or nerves caused by the electrostimulation delivered using an electrostimulation vector. In an example, the complication analysis circuit 613 can detect the phrenic nerve activation such as by using an accelerometer or other sensors during delivery of cardiac electrostimulation using an electrostimulation vector. The presence or absence of phrenic nerve activation in response to the electrostimulation at a specified level can be detected by comparing the accelerometer signal intensity to a threshold value. Detection of the phrenic nerve activation can also include determining one or more parameters including a phrenic nerve stimulation threshold ($PNS_T$) representing minimum stimulation energy sufficient to elicit phrenic nerve activation, or a safety margin for phrenic nerve activation, which can be determined as a relationship between the $PNS_T$ and the cardiac capture threshold.

The electrostimulation vector assessment circuit 620 can include a first comparator circuit 621 to compare the MI indicators of the plurality of candidate electrostimulation vectors, and at least a second comparator circuit (such as one or more of comparator circuits 622, 623 and 624) to compare at least one of the one or more second indicators of the candidate electrostimulation vectors. For example, the comparator circuit 622 can compare the therapy efficacy indicators of the candidate electrostimulation vectors, the comparator circuit 623 can compare the battery longevity indicators of the candidate electrostimulation vectors, and the comparator circuit 624 can compare the complication indicators of the candidate electrostimulation vectors.

The selectable/rankable vector generation circuit 625 can produce a selectable set or a rankable set of at least some of the plurality of candidate electrostimulation vectors, along with the respective MI indicators and one or more of the therapy efficacy indicators, battery longevity indicators, and the complication indicators. The selectable/rankable vector generation circuit 625 can select, automatically or based on a user input, at least one target electrostimulation vector from the candidate electrostimulation vectors using the respective MI indicators and the respective one or more second indicators. In an example, the selectable/rankable vector generation circuit 625 can select a target electrostimulation vector associated with (1) a MI indicator indicating the selected target electrostimulation vector does not involve an electrostimulation electrode proximal to a MI tissue, and (2) a therapy efficacy indicator indicating a longer inter-ventricular delay associated with electrostimulation according to the selected target electrostimulation vector than electrostimulation according to other of the plurality of candidate electrostimulation vectors. In an example, the selectable/rankable vector generation circuit 625 can rank at least some of the candidate electrostimulation vectors using the comparison of the MI indicators and the comparison of the at least one of the one or more second indicators, such as produced by the comparators 621-624. Ranking of the candidate electrostimulation vectors can include first generating first ranked vectors by ranking the at least some candidate electrostimulation vectors according to a first specified order of first specified indicators, and then generating at least second ranked vectors by ranking at least a portion of the first ranked vectors according to a second specified order of second specified indicators different from the first specified indicators, wherein the portion of the first ranked vectors have corresponding first indicators meeting a specified condition. The first and second specified indicators can be selected from MI indicators, therapy efficacy indicators, battery longevity indicators, or complication indicators.

In an example, the selectable/rankable vector generation circuit 625 can select at least one unipolar electrostimulation vector and at least one bipolar electrostimulation vector. A unipolar electrostimulation vector can involve an electrode positioned at or near a target stimulation site of the heart (such as an electrode on one of the leads 108A-C), and a return electrode such as the IMD can 112. For example, a unipolar LV electrostimulation vector can involve a cathode being an LV electrode, such as one of the electrodes 161-164 along the LV lead 108C, and an anode being the IMD can 112. A bipolar electrostimulation vector, such as a bipolar LV electrostimulation vector, can involve a cathode and an anode both positioned at or near the LV (such as the electrodes 161-164 along the LV lead 108C), or one of the cathode or anode being an LV electrode and the other of the cathode or anode being placed on a different chamber or on a different lead (such as one of electrodes 152-155 on the RV lead 108B, or electrodes 141 or 142 on the RA lead 108A). The selectable/rankable vector generation circuit 625 can first select at least one unipolar LV electrostimulation vector from a plurality of candidate unipolar LV electrostimulation vectors using the respective MI indicators and one or more of the therapy efficacy indicators, battery longevity indicators, and the complication indicators. The selectable/rankable vector generation circuit 625 can then screen a plurality of candidate bipolar LV electrostimulation vectors by identifying those vectors that involve a cathode or an anode that is also involved in a selected unipolar LV electrostimulation vector. The selectable/rankable vector generation circuit 625 can then rank or select the identified bipolar LV electrostimulation vectors using the using the MI indicators and one or more of the therapy efficacy indicators, battery longevity indicators, and the complication indicators corresponding to the identified bipolar LV electrostimulation vectors.

FIGS. 7A and 7B illustrate generally examples of display of electrostimulation vectors and various corresponding indicators. The display can be a part of the information presented in the output circuit 252 of the user interface unit 250. Although the electrostimulation vectors and the corresponding indicators are presented in a table as illustrated in FIGS. 7A-B, other textual or graphical presentation formats can alternatively or additionally be used. In FIG. 7A, the display includes a table 700A showing, for each of a plurality of candidate electrostimulation vectors 710, the MI indicator 721, a therapy efficacy indicator 722, a longevity indicator 723, and a complication indicator 724. The MI indicators 721 include categorical values of "distal/absence" indicating no detection of MI or the corresponding electrostimulation vector being proximal to MI; or "proximal" indicating presence of a MI which is proximal to the corresponding electrostimulation vector. Other categorical values, such as "Yes" (to indicate presence of MI) or "No" (to indicate absence of MI) can be used. The therapy efficacy indicator 722 can be a numerical or a categorical value determined using one or more electrical or mechanical signal metrics, such as inter-ventricular delay, intra-ventricular delay, or cardiac timing interval. In the example as shown in FIG. 7A, a higher number indicates a more effective therapy. The longevity indicator 723 can be a numerical or a categorical value determined using one or more measurements such as the capture threshold or lead impedance. In the example as shown in FIG. 7A, the longevity indicators are represented by the remaining battery life in years. The complication indicator 724 can be a numerical or a categorical value determined using one or more measurements such as the PNS threshold, skeletal muscle activity strength, among others. In the example as shown in FIG. 7A, the complication indicators are represented by the remaining battery life in years.

In FIG. 7B, the display includes a table 700B showing, for each of a list of electrostimulation vectors 710, one or more individual measurements, or signal metrics, that are related to the MI indicators, the therapy efficacy indicator, the battery longevity indicator, or the complication indicator. For example, the measurements or signal metrics related to MI indicators can include amplitude or other intensity measurements of cardiac depolarization, timings of the depolarization, among others. As illustrated in FIG. 7B, these measurements or signal metrics can include: LV amplitude 731 that is related to the MI indicator; RV-LV delay 732, or Q-LV delay 733 that are related to the therapy efficacy indicator; capture threshold 734, lead impedance 735, and estimated battery life 736 that are related to the longevity indicator; and PNS threshold 737 that is related to the complication indicator.

The indicators 721-724, or the measurements or signal metrics 731-737, can each be provided in the display with a sorting control button 720 that enables a system user to sort the electrostimulation vectors according to an ascending order (such as by selecting or clicking on an icon "Δ") or a descending order (such as by selecting or clicking on an icon "∇"). The electrostimulation vectors 710 can be provided in the display with a selection control button 711 for manually selecting a target stimulation vector, or confirming an automatically selected target stimulation vector (denoted by an icon "√" inside a selection box). Additionally, the electrostimulation vectors 710 can also include a sorting option 720 for sorting the candidate stimulation vectors such as according to a specified order of electrode being involved. In an example, the sorting options on the display 700A or 750B can enable a system user to perform multi-level ranking on at least some of the candidate electrostimulation vectors, such as by generating first ranked vectors according to a first specified order of first specified indicators, and then generate second ranked vectors by ranking at least a portion of the first ranked vectors according to a second specified order of second specified indicators. The portion of the first ranked vectors has corresponding first indicators that meet a specified condition.

In some examples, the indicators 721-724 in FIG. 7A, or the measurements or signal metrics 731-737 in FIG. 7B, can be displayed in more than one table. For example, some of the indicators 721-724 can be displayed in a first table, and other of the indicators 721-724 can be displayed in a different second table. Similarly, some of the signal metrics 731-737 can be displayed in a first table, and other of the signal metrics 731-737 can be displayed in a different second table. The table, or other presentation format, can be presented at different time, such as before or after a system user makes a selection. For example, during testing of a particular candidate stimulation vector, an alert (such as in a message window) can be displayed showing the candidate stimulation vector having a MI indicator of being "proximal" to a MI tissue. The system user can select or deselect that candidate stimulation vector for inclusion in a table. In another example, after a candidate electrostimulation vector is selected, an alert can be displayed if the selected vector has a MI indicator of being "proximal" to a MI tissue.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
    a physiologic sensor circuit, including a sense amplifier circuit to sense respective physiologic signals at three or more candidate stimulation sites at or within at least one chamber of a heart of a patient;
    an activation timer circuit, including a clock circuit coupled to the physiologic sensor circuit to use the sensed respective physiologic signals to produce respective activation timing indicators corresponding to the three or more candidate stimulation sites;
    a myocardial infarction (MI) receiver circuit to receive respective MI indicators indicating relative spatial proximity of each of the three or more candidate stimulation sites to a MI tissue; and
    a stimulation site selector circuit, communicatively coupled to the activation timer circuit and the MI receiver circuit, configured to select a stimulation site from the three or more candidate stimulation sites associated with the respective MI indicators using the respective activation timing indicators and the respective MI indicators as the candidate stimulation site associated with and spatially more remote to the MI tissue than other of the three or more candidate stimulation sites.

2. The system of claim 1, comprising a therapy circuit configured to deliver electrostimulation to the patient using the selected stimulation site.

3. The system of claim 2, wherein:
    the stimulation site selector circuit is configured to select a first stimulation site and a different second stimulation site from the three or more candidate stimulation sites using the respective activation timing indicators and the respective MI indicators;
    the therapy circuit is configured to deliver the electrostimulation at the first and the second stimulation sites during a same cardiac cycle.

4. The system of claim 1, wherein:
    the physiologic sensor circuit is configured to sense the respective physiologic signals including cardiac electrical signals sensed at three or more left-ventricular (LV) candidate sites of the heart; and
    the activation timer circuit is configured to determine the respective activation timing indicators including respective depolarization timings at the three or more LV candidate sites.

5. The system of claim 4, wherein the physiologic sensor circuit is configured to sense the cardiac electrical signals including intrinsic or evoked depolarizations at the three or more LV candidate sites, the evoked depolarizations produced in response to a stimulation of the heart.

6. The system of claim 4, wherein the activation timer circuit is configured to determine the respective depolarization timings including time intervals between a reference time and the respective depolarizations at the three or more LV candidate sites.

7. The system of claim 1, comprising a MI detector circuit, coupled to the physiologic sensor circuit, configured to detect the respective MI indicators at the three or more candidate stimulation sites using the respective physiologic signals including cardiac electrical signals at three or more LV candidate sites.

8. The system of claim 7, wherein the MI detector circuit includes a level detector circuit configured to determine, for each of the three or more LV candidate sites, an amplitude of the cardiac electrical signal sensed at the corresponding LV candidate site, wherein the MI detector circuit is configured to determine the relative spatial proximity to the MI tissue at the corresponding LV candidate site based on the corresponding amplitude of the cardiac electrical signal.

9. The system of claim 8, wherein the MI detector circuit includes a comparator circuit configured to compare the amplitudes of the cardiac electrical signals to a threshold, wherein the MI detector circuit is configured to detect, for each of the three or more LV candidate sites, a respective MI indicator as one of:
 a first indicator of being spatially proximal to a MI tissue if the determined amplitude falls below the threshold; or
 a second indication of being spatially remote to, or absence of, a MI tissue if the determined amplitude exceeds the threshold.

10. The system of claim 1, wherein the stimulation site selector is configured to select the stimulation site further associated with the respective activation timing indicator indicating a later activation than other of the three or more candidate stimulation sites.

11. The system of claim 1, wherein the stimulation site selector circuit is configured to generate a selectable set of candidate electrostimulation vectors including an electrode positioned at the selected stimulation site.

12. The system of claim 1, further comprising:
 a secondary indicator generation circuit configured to generate one or more second indicators indicative of one of therapy efficacy, battery longevity, or complication of stimulation; and
 a user interface that enables a user to perform one of more of:
 ranking at least some of the candidate electrostimulation vectors according to an order of the MI indicators or the one or more second indicators;
 selecting at least one target electrostimulation vector from the candidate electrostimulation vectors; or
 programming an electrostimulation therapy for delivery at the heart according to the selected at least one target electrostimulation vector.

13. A system, comprising:
 a physiologic sensor circuit, including a sense amplifier circuit to sense cardiac electrical signals at three or more candidate stimulation sites in a left ventricle (LV) of a heart of a patient;
 an activation timer circuit, including a clock circuit coupled to the physiologic sensor circuit to use the sensed cardiac electrical signals to produce respective activation timing indicators corresponding to the three or more LV candidate sites;
 a myocardial infarction (MI) detector circuit, including:
 a level detector circuit configured to determine, for each of the three or more LV candidate sites, a relative spatial proximity to MI tissue based on an amplitude of the cardiac electrical signal sensed at the corresponding LV candidate site; and
 a comparator circuit configured to compare the amplitudes of the cardiac electrical signals to a threshold to detect, for each of the three or more LV candidate sites, a respective MI indicator as one of a first indicator of being spatially proximal to a MI tissue if the determined amplitude falls below the threshold, or a second indication of being spatially remote to, or absence of, a MI tissue if the determined amplitude exceeds the threshold;
 a stimulation site selector circuit configured to select at least one stimulation site from the three or more candidate stimulation sites associated with the respective MI indicators using (1) a respective activation timing indicator indicating a later activation than other of the three or more candidate stimulation sites, and (2) a respective MI indicator indicating spatially more remote to a MI tissue than other of the three or more candidate stimulation sites, the selected at least one stimulation site associated with the MI tissue; and
 a therapy circuit, configured to deliver electrostimulation to the patient using the selected at least one stimulation site.

14. A method, comprising:
 sensing, at three or more candidate stimulation sites at or within at least one chamber of a heart of a patient, respective physiologic signals;
 determining respective activation timing indicators corresponding to the three or more candidate stimulation sites by using the sensed respective physiologic signals;
 detecting respective myocardial infarction (MI) indicators indicating relative spatial proximity of each of the three or more candidate stimulation sites to, a MI tissue; and
 selecting a stimulation site from the three or more candidate stimulation sites associated with the respective MI indicators using the respective activation timing indicators and the respective MI indicators as the candidate stimulation site associated with and spatially more remote to the MI tissue than other of the three or more candidate stimulation sites.

15. The method of claim 14, further comprising delivering electrostimulation using the selected stimulation site.

16. The method of claim 15, comprising:
 selecting at least a first stimulation site and a different second stimulation site from the three or more candidate stimulation sites using the respective activation timing indicators and the respective MI indicators; and
 delivering the electrostimulation includes delivering respective electrostimulation at the first and the second stimulation sites during a same cardiac cycle.

17. The method of claim 14, wherein:
 sensing the respective physiologic signals includes sensing cardiac electrical signals at three or more left-ventricular (LV) candidate sites of the heart; and
 determining the respective activation timing indicators includes determining respective depolarization timings at the three or more LV candidate sites.

18. The method of claim 14, wherein:
 sensing the respective physiologic signals includes sensing cardiac electrical signals at three or more left-ventricular (LV) candidate sites of the heart;
 determining the respective MI indicators includes:
 determining the relative spatial proximity to the MI tissue based on amplitudes of the cardiac electrical signals sensed at the three or more LV candidate sites; and
 detecting, for each of the three or more LV candidate sites, a respective MI indicator as one of a first indicator of being spatially proximal to a MI tissue if the amplitude falls below a threshold, or a second indication of being spatially remote to, or absence of, a MI tissue if the amplitude exceeds the threshold.

19. The method of claim 14, wherein the selected stimulation site is further associated with an activation timing indicator indicating a later activation than other of the three or more candidate stimulation sites.

20. The method of claim 14, further comprising:
generate one or more second indicators indicative of one of therapy efficacy, battery longevity, or complication of stimulation;
generating a selectable set of candidate electrostimulation vectors including an electrode positioned at the selected stimulation site; and
ranking, automatically or based on a user input, at least some of the candidate electrostimulation vectors according to an order of the MI indicators or the one or more second indicators.

* * * * *